United States Patent
Jackson et al.

(10) Patent No.: US 11,422,355 B2
(45) Date of Patent: Aug. 23, 2022

(54) METHOD AND SYSTEM FOR ACQUISITION OF FLUORESCENCE IMAGES OF LIVE-CELL BIOLOGICAL SAMPLES

(71) Applicant: Sartorius BioAnalytical Instruments, Inc., Bohemia, NY (US)

(72) Inventors: Timothy Jackson, Ann Arbor, MI (US); Rickard Sjögren, Ann Arbor, MI (US); Christoffer Edlund, Ann Arbor, MI (US); Edvin Forsgren, Ann Arbor, MI (US)

(73) Assignee: Sartorius BioAnalytical Instruments, Inc., Bohemia, NY (US)

(*) Notice: Subject to any disclaimer, the term of this patent is extended or adjusted under 35 U.S.C. 154(b) by 176 days.

(21) Appl. No.: 16/935,326

(22) Filed: Jul. 22, 2020

(65) Prior Publication Data
US 2022/0026699 A1     Jan. 27, 2022

(51) Int. Cl.
*G02B 21/36*     (2006.01)
*G02B 21/34*     (2006.01)
(Continued)

(52) U.S. Cl.
CPC ......... *G02B 21/367* (2013.01); *C12N 5/0693* (2013.01); *C12N 5/0697* (2013.01);
(Continued)

(58) Field of Classification Search
CPC ...... G02B 21/34; G02B 21/16; G02B 21/367; G06T 2207/10056; G06T 7/571;
(Continued)

(56) References Cited

U.S. PATENT DOCUMENTS

2013/0010160 A1   1/2013   Kawamura
2019/0025213 A1*   1/2019   Abe .................... G02B 21/367
(Continued)

FOREIGN PATENT DOCUMENTS

EP           2687892 A1     1/2014
WO      2020139835 A1     7/2020
WO   WO2020139835 A1 *   7/2020   ............. G01N 15/14

OTHER PUBLICATIONS

International Search Report and Written Opinion for corresponding PCT application No. PCT/US2021/039808, dated Oct. 18, 2021.
(Continued)

*Primary Examiner* — Frantz B Jean
(74) *Attorney, Agent, or Firm* — McDonnell Boehen Hulbert & Berghoff LLP (57) ABSTRACT

A method is disclosed for acquiring a single, in-focus two-dimensional projection image of a live, three-dimensional cell culture sample, with a fluorescence microscope. One or more long-exposure "Z-sweep" images are obtained, i.e. via a single or series of continuous acquisitions, while moving the Z-focal plane of a camera through the sample, to produce one or more two-dimensional images of fluorescence intensity integrated over the Z-dimension. The acquisition method is much faster than a Z-stack method, which enables higher throughput and reduces the risk of exposing the sample to too much fluorescent light. The long-exposure Z-sweep image(s) is then input into a neural network which has been trained to produce a high-quality (in-focus) two-dimensional projection image of the sample. With these high-quality projection images, biologically relevant analysis metrics can be obtained to describe the fluorescence signal using standard image analysis techniques, such as fluorescence object count and other fluorescence intensity metrics (e.g., mean intensity, texture, etc.).

34 Claims, 8 Drawing Sheets

(51) Int. Cl.
| | |
|---|---|
| *G06T 7/571* | (2017.01) |
| *C12N 5/09* | (2010.01) |
| *C12N 5/071* | (2010.01) |
| *G01N 21/64* | (2006.01) |
| *G01N 33/50* | (2006.01) |
| *G02B 21/16* | (2006.01) |
| *G06N 3/04* | (2006.01) |
| *G06N 3/08* | (2006.01) |
| *G06T 15/08* | (2011.01) |
| *H04N 5/235* | (2006.01) |

(52) U.S. Cl.
CPC ..... *G01N 21/6428* (2013.01); *G01N 21/6458* (2013.01); *G01N 33/5005* (2013.01); *G02B 21/16* (2013.01); *G02B 21/34* (2013.01); *G06N 3/0454* (2013.01); *G06N 3/088* (2013.01); *G06T 7/571* (2017.01); *G06T 15/08* (2013.01); *H04N 5/2353* (2013.01); *C12N 2503/00* (2013.01); *C12N 2513/00* (2013.01); *G01N 2021/6439* (2013.01); *G06T 2207/10056* (2013.01); *G06T 2207/10064* (2013.01); *G06T 2207/20081* (2013.01); *G06T 2207/20084* (2013.01); *G06T 2207/30024* (2013.01); *G06T 2207/30072* (2013.01)

(58) Field of Classification Search
CPC ........... G06T 2207/10064; G06T 15/08; G06T 2207/20084; G06T 2207/20081; G06T 2207/30024; G06T 2207/30072; H04N 5/2353; G06N 3/0454; G06N 3/088; C12N 2503/00; C12N 5/0693; C12N 5/0697; C12N 2513/00; G01N 33/5005; G01N 21/6428; G01N 2021/6439; G01N 21/6458
USPC .......................................................... 348/79
See application file for complete search history.

(56) References Cited

U.S. PATENT DOCUMENTS

| | | |
|---|---|---|
| 2019/0121112 A1 | 4/2019 | Kitagawa et al. |
| 2019/0137394 A1 | 5/2019 | Kaneko |
| 2019/0333199 A1 | 10/2019 | Ozcan et al. |
| 2020/0167914 A1 | 5/2020 | Stamatoyannopoulos et al. |

OTHER PUBLICATIONS

Kuen He et al: "Computational Multifocal Microscopy", arxiv.org, Cornell University Library, 201 Olin Library Cornell University Ithica, NY 14853, Sep. 4, 2018, XP081187236, Section 1, 1.2; figure 1.

Marti Duocastella et al: "Simultaneous Multiplane Confocal Microscopy Using Acoustic Tunable Lenses", Optics Express, vol. 22, No. 16, Aug. 11, 2014, p. 19293, XP055517404, US IISN 2161-2072, DOI: 10,1364/OE.22.019293.

U.S. patent application of Timothy Jackson et al., U.S. Appl. No. 16/854,710, filed Apr. 21, 2020, entitled "Image Processing and Segmentation of Sets of Z-Stacked Images of Three-Dimensional Biological Samples".

US patent application of Brad Neagle et al., U.S. Appl. No. 16/854,756, filed Apr. 21, 2020, entitled "Optical module with three or more color fluorescent light sources and methods for use thereof".

Weigert, Martin et al. "Content-Aware Image Restoration: Pushing the Limits of Fluorescence Microscopy" bioRxiv Jul. 3, 2018.

Woringer et al. "Faster and less phototoxic 3D fluorescence microscopy using a versatile compressed sensing scheme" Optics Express (2017) vol. 25(12), pp. 13668-13683.

Fu, Chichen et al. "Three Dimensional Fluorescence Microscopy Image Synthesis and Segmentation" arXiv:1801.07198 [cs.CV] (2018).

Wu, Yichen et al. "Three-dimensional virtual refocusing of fluorescence microscope images using deep learning" Nature Methods (2019) vol. 16, pp. 1323-1331.

Weigert, Martin et al. "Isotropic reconstruction of 3D fluorescence microscopy images using convolutional neural networks" arXiv:1704.01510 [cs.CV] (Apr. 5, 2017).

Schneider, C. A., Rasband, W. S., & Eliceiri, K. W. (2012). NIH Image to ImageJ: 25 years of image analysis Nature methods, 9(7), 671-675.

Goodfellow et al. "Generative Adversarial Nets," in Advances in Neural Information Processing Systems 27, Z. Ghahramani, M. Welling, C. Cortes, N. D. Lawrence, and K. Q. Weinberger, Eds. Curran Associates, Inc., 2014, pp. 2672-2680.

Ronneberger, et al. "U-net: Convolutional networks for biomedical image segmentation", arXiv: 1505.04597 (2015).

Jun-Yan Zhun et al. "Unpaired image-to-image translation using cycle-consistent adversarial networks", arXiv:1703.10593 (2017).

Philip Isola et al., Image-to Image Translation with Conditional Adversarial Networks, arXiv.1611.07004 [cv.cs] (2016).

Xudong Mao, et al., Least Squares Generative Adversarial Networks, arXiv.1611.04076 [cv.cs] (2016).

* cited by examiner

Z-Sweep Acquisition

FIG. 2B

Consecutive Z-Sweep Acquisition

FIG. 2C
PRIOR ART

Z-Stack Acquisition

METHOD AND SYSTEM FOR ACQUISITION OF FLUORESCENCE IMAGES OF LIVE-CELL BIOLOGICAL SAMPLES

BACKGROUND

This disclosure relates to the field of methods and systems for obtaining fluorescence images of live-cell biological samples, for example three-dimensional (3D) cell cultures including organoids and tumor spheroids.

The use of live-cell samples spans a wide variety of research areas, including immuno-oncology, oncology, metabolism, neuroscience, immunology, infectious disease, toxicology, stem cell, cardiology and inflammation. In these research areas, studies are made of cell health and proliferation, cell function, cell movement and morphology, including the study of complex immune-tumor cell interactions, synaptic activity, metabolism in cancer cells, and much more.

Fluorescence microscopy is a method of observing photoemissive spectra from samples, including live-cell samples. Observing the fluorescence from the sample requires an optical system including an incident light source and optical filters with out-of-band rejection parameters. This setup enables researchers to perform real-time analysis of a sample's fluorescent qualities. Fluorescence microscopes which include imaging functionality (by means of a camera or imager of various designs) are now part of the modern live-cell research laboratory.

In fluorescence microscopy, it is customary for the sample to be treated, stained, or chemically compounded with one or more fluorophores. Fluorophores are microscopic molecules, which may be proteins, small organic compounds, organic dyes, or synthetic polymers, that absorb light of specific wavelengths and emit light of longer wavelengths. Certain semiconducting metallic nanoparticles also qualify as fluorophores, emitting light relative to their geometric composition.

Live-cell biological samples can be microscopically imaged in a fluorescence microscope, typically at some magnification such as 10× or 20×, in a variety of ways in order to assess the growth, metabolism, morphology, or other properties of the sample at one or more points in time. This microscopic imaging can include fluorescence imaging, wherein fluorophores in the sample are excited by light at excitation wavelength(s) of the fluorophores, causing them to fluorescently emit light at emission wavelength(s) of the fluorophores. In epifluorescence imaging, the excitation light is provided via the same objective that is used to collect to the emission light.

The overall trend of biological research has been leaning toward the importance of studying of 3D models (e.g., tumor spheroids, organoids, 3D cell cultures) as opposed to their two-dimensional (2D) counterparts (e.g., a single image in a given focal plane) because it is believed that 3D models better replicate the physiological conditions that exist in true in vivo systems.

The standard methods of obtaining 3D information of a sample using a fluorescence or confocal microscope involve a step-wise "Z-stacking" method, in which a series of images of a sample are captured, each at a particular depth or Z coordinate of the sample in a three dimensional coordinate system. This methodology is shown in FIG. 2C of this disclosure and will be described in more detail later. The resulting series of images can then be manipulated using special software to project or combine the images into a single 2D Image. One method for making this Z projection is set forth U.S. patent application of Timothy Jackson et al., "Image Processing and Segmentation of Sets of Z-Stacked Images of Three-Dimensional Biological Samples", Ser. No. 16/854,710 filed Apr. 21, 2020, assigned to the assignee of this invention, the description of which is incorporated by reference herein. An example of an open source image analysis software package to project the Z-stack images into a 2D image is ImageJ, which is described in Schneider, C. A., Rasband, W. S., & Eliceiri, K. W. (2012). *NIH Image to ImageJ: 25 years of image analysis*. Nature methods, 9(7), 671-675. There are several Z-projection schemes including maximum projection, average projection, Sobel filter based projection, and wavelet based projection.

The Z-stacking method, however, can have several inherent challenges, and problems, particularly for live-cell samples. First, the requirement to fine-tune different acquisition parameters, including exposure time, starting Z-location, ending Z-location, Z-step (A Z increment between image capture locations), etc., requires knowledge of the sample in advance which is only possible for an expert-level user. Second, the time to acquire such images can become so onerously slow that it limits throughput and exposes the sample to a large amount of fluorescent light from the light source, which could cause photobleaching or phototoxicity of the sample, which are highly undesirable in live-cell studies. Finally, acquiring 3D Z-stacks then requires advanced software to visualize and analyze the data.

SUMMARY

This document describes a method and system including an image acquisition strategy and image processing procedure using deep learning to address the above imaging challenges. In particular, described herein are methods to acquire a single, in-focus 2D projection of a 3D live-cell biological sample, in a high-throughput manner, utilizing recent advancements in deep learning and convolutional neural networks.

Instead of using the known Z-stack strategy, one or more long-exposure "Z-sweep" images are obtained, i.e., a single or series of consecutive, long exposure continuous image acquisitions, in which a camera in a fluorescence microscope is exposed to the sample while moving the Z-focal plane through the sample, thereby integrating fluorescence intensity from the sample over the Z-dimension. The acquisition method is much faster than a Z-stack, and thus enables higher throughput and reduces the risk of exposing the sample to too much fluorescent light, thereby avoiding problems with phototoxicity and photobleaching. The long-exposure image(s) is then input into a trained neural network, which is trained to produce a high-quality, in focus 2D projection image which represents a projection of the 3D sample. With these high-quality 2D projection images, biologically relevant analysis metrics that describe the fluorescence signal using standard image analysis techniques can be obtained, such as fluorescence object count and other fluorescence intensity metrics (e.g., mean intensity, texture, etc.).

In one specific aspect, a method is provided for generating an in-focus two-dimensional projection of a fluorescence image of a three-dimensional live-cell sample. The method includes the steps of: acquiring with a camera, one or more long exposure images of the sample by moving a focal plane of the camera through the sample in a Z direction, the camera thereby integrating fluorescence intensity from the sample over a Z-dimension, supplying the one or more long exposure images to a neural network model trained from a plurality training images; and generating with the neural network model an in-focus 2D projection image.

Several different types of neural network models are possible. In one embodiment, the neural network model is a convolutional neural network, and in another embodiment an encoder-decoder based supervised model. The encoder-decoder based supervised model may take the form of U-net, described in the literature as explained below. Alternatively, the neural network model is trained using an adversarial approach such as the case with generative adversarial networks (GANs). See Goodfellow et al., "Generative Adversarial Nets," in Advances in Neural Information Processing Systems 27, Z. Ghahramani, M. Welling, C. Cortes, N. D. Lawrence, and K. Q. Weinberger, Eds. Curran Associates, Inc., 2014, pp. 2672-2680. This adversarial approach means that two neural networks are trained simultaneously: a generator predicting a high-quality in-focus projection image, and a discriminator trying to distinguish between predicted in-focus projection images and real or actual acquired images. The advantage of this approach is that the adversarial training may result in more realistic outputs compared to ordinary supervised training due to the generator trying to fool the discriminator. A conditional GAN, where the generator is conditioned on the one or more long exposure images, is another possibility. The neural network model may also be trained with a cycle consistency loss methodology making it possible to train with unpaired data, such as with GANs or CycleGAN (GAN with cycle consistency loss), which is also described in the literature. Unpaired data means that there are Z-sweep images and in-focus projection images, but not necessarily any pair with one-to-one pixel matching. The advantage of the cycle consistency approach is that it does not require perfect registration between the Z-sweeps and in-focus projection images. Imperfect registration may for instance occur when there is slight movement in X-Y plane when the camera is moved along the Z-axis.

Three different ways or paradigms are contemplated for generating the one or more long exposure Z-sweep images. In one configuration, a single long exposure Z-sweep image is obtained, referred to as "paradigm 1" below. Alternatively, a series of long exposure consecutive Z-sweep images are obtained, which are then summed, referred to as "paradigm 2" below. As another alternative, a series of long exposure consecutive Z-sweep images are obtained which are not summed, referred to as "paradigm 3" below.

In another aspect, a method of training a neural network model to generate an in-focus 2D projection image of a live-cell sample is disclosed. The method includes the step of obtaining a training set in the form of a multitude of images. Such images could be pairs of images, or unpaired images. In practice it is beneficial to have pairs, particularly if the neural network model uses supervised training. However the use of unpaired images is possible, for example with cycle-consistency loss training, or generative adversarial networks.

The training images can include (1) one or more long exposure Z-sweep images of a live-cell sample obtained by moving a focal plane of a camera through the sample in a Z direction, the camera thereby integrating fluorescence intensity from the sample over the Z-dimension, and (2) an associated two-dimensional Z-stack projection ground truth image, wherein the ground truth image is obtained from a set of Z-stack images of the same live-cell sample, each of the images of the Z-stack images obtained at a different Z focal plane position of the sample, and wherein the Z-stack images are combined using a Z-projection algorithm. The method further includes the step of conducting a training procedure of the neural network from the training set and thereby generating a model which is trained to ultimately generate a 2D projection image of a live-cell sample from input in the form of one or more long exposure Z-sweep images.

As noted above, the long exposure Z-sweep images in the training set can take the form of a single Z-sweep image or a set of a set of consecutive Z-sweep images, optionally summed, or some combination of any of the three acquisition paradigms.

In still another aspect, a live cell imaging system is described for use in conjunction with a sample holding device, e.g., microwell plate, adapted for holding a live-cell sample. The system includes a fluorescence microscope having one or more excitation light sources, one or more objective lenses, and a camera operable to obtain fluorescence images from the live-cell sample held within the sample holding device. The fluorescence microscope includes a motor system configured to move the fluorescence microscope relative to the sample holding device including in the Z direction such that the camera obtains one or more long exposure Z-sweep images of the sample, the one or more Z-sweep images obtained by moving a focal plane of a camera through the sample in a Z direction. The system further includes a processing unit including a neural network model trained to generate an in-focus two dimensional projection of a fluorescence image of the live-cell sample from the one or more long exposure Z-sweep images.

In still another aspect, a method is provided for generating a training set for training a neural network. The method includes steps of: (a) with a camera, acquiring one or more long exposure fluorescence images of a three-dimensional sample by moving a focal plane of the camera through the sample in a Z direction, the camera thereby integrating fluorescence intensity from the sample over a Z-dimension; (b) generating a ground truth image of the same sample from one or more different images of the sample obtained by the camera; (c) repeating steps (a) and (b) for a multitude of different samples; and (d) supplying the images acquired by performing steps (a), (b) and (c) as a training set for training a neural network.

The methods of this disclosure have a number of benefits:

(1) The method allows one to obtain biologically relevant analysis metrics from the high-quality projection images using standard image analysis techniques, such as fluorescence object count or other fluorescence intensity metrics.

(2) The one or more long exposure images is a true representation of the fluorescence in the sample integrated over the Z-dimension, resulting in generation of true, accurate data.

(3) The methods of this disclosure can be implemented without any changes to the hardware of a conventional motorized fluorescence microscope.

(4) While the workflow of this disclosure is designed to accommodate traditional wide-field fluorescence microscopy, it can be applied to spinning disk confocal microscopy to improve the throughput of that modality as well.

(5) The method provides as an output a single, high-quality 2D projection image, which eliminates the onus on the user to have complicated software and analysis tools to handle a 3D dataset. The 2D projection images can be input into standard 2D image visualization, segmentation, and analysis pipelines, for example those that are currently implemented in state of the art fluorescence microscope platforms on the market today.

In still another aspect, a computer-readable medium is provided which stores non-transient instructions for a live-cell imaging system including a camera and a processing unit implementing a neural network model, the instructions causing the system to perform the methods of this disclosure, for example combination of capturing the one or more long exposure Z-sweep images of a sample, supplying the image to a trained neural network model, and generation of a two-dimensional projection image with the trained neural network model.

BRIEF DESCRIPTION OF THE DRAWINGS

FIG. 3 also illustrates a method of acquiring a new input image for inference using the trained neural network model and the output in the form of a high quality 2D projection image.

In FIG. 9, the neural network model was a trained conditional generative adversarial network (GAN) and the input images were generated under the second image acquisition paradigm of FIG. 3.

DETAILED DESCRIPTION

Figure 1:
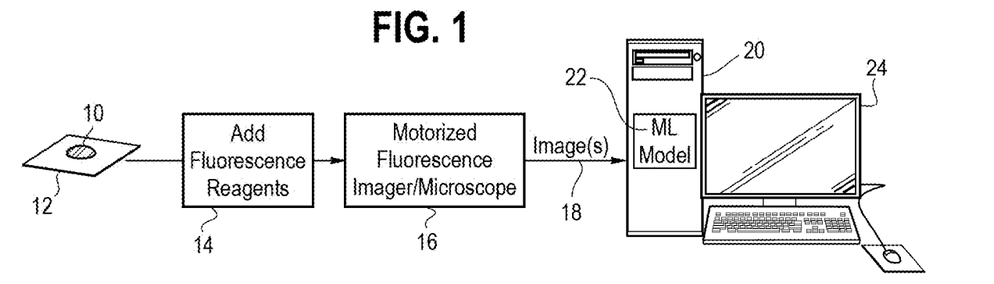
FIG. 1 is a schematic illustration of a method and system for acquisition of 3D fluorescence images of live-cell biological samples.

Referring now to FIG. 1, a live-cell biological sample (which may take the form of any of the types of live-cell samples used in current research, as mentioned in the Background, such as a live, three-dimensional cell culture) is placed on or in a suitable holding structure 12, for example a microwell plate or glass slide. One or more fluorescence reagents (fluorophores) may be added to the live-cell sample 10, as indicated at 14, the type or nature of the fluorescence reagents will of course depend on the particulars of the sample 10 and the nature of the research being conducted. The holding structure 12 with sample 10 and reagents is then supplied to a motorized fluorescence microscope 16 having a camera, which may take the form of any of the conventional fluorescence microscopes with imaging functionality known in the art or available from many manufacturers, including the assignee of this invention.

Figure 2A:
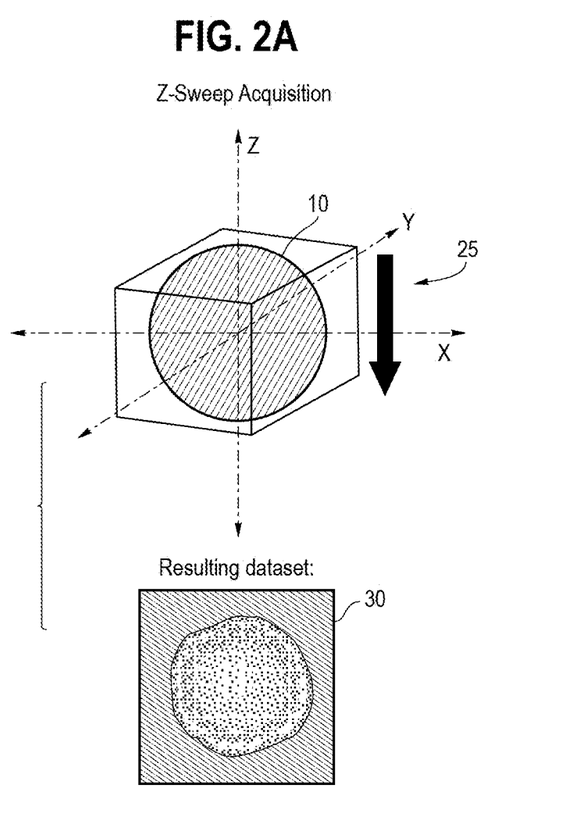
FIG. 2A is an illustration of a Z-sweep image acquisition method which can be used in the motorized fluorescence microscope of FIG. 1.
Figure 2B:
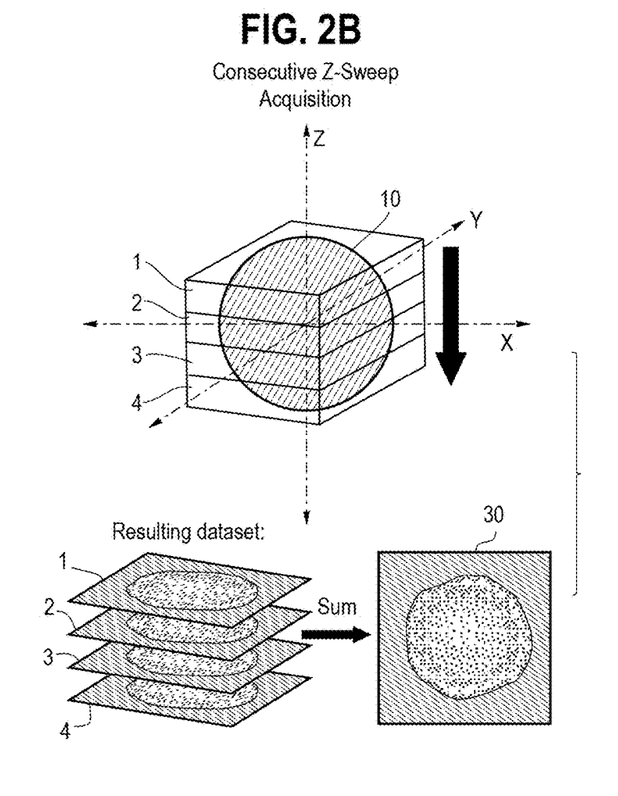
FIG. 2B is an illustration of a consecutive Z-sweep image acquisition method.
Figure 2C:
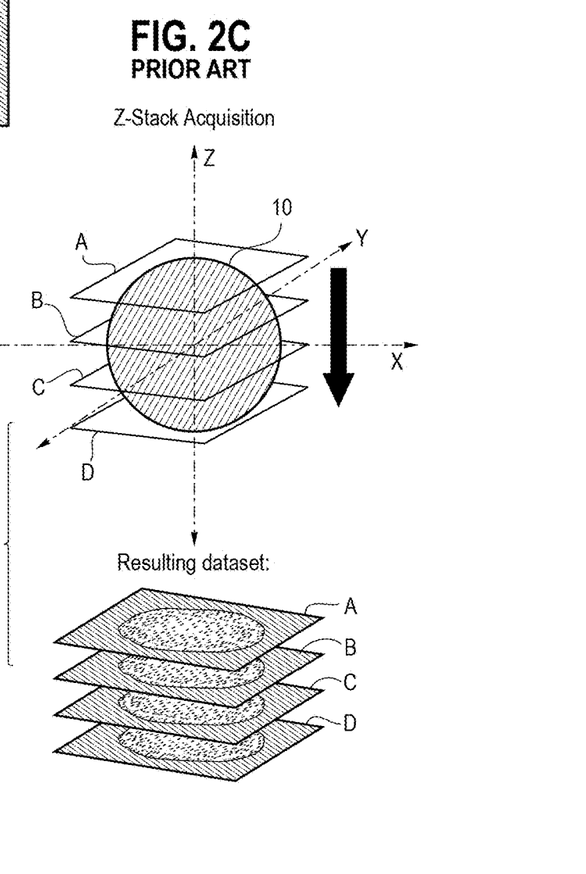
FIG. 2C is an illustration of a prior art Z-stack image acquisition method.

The fluorescence microscope 16 is used to generate one or more long exposure Z-sweep images (or a set of such images) 18 in accordance with the methodology of FIG. 2A or 2B. This long exposure Z-sweep image of the 3D live-cell biological sample 10 is obtained by moving a focal plane of a camera in the microscope through the sample in a Z direction, as indicated at 25 in FIG. 2A and in FIG. 6 at 25, in which the camera integrates fluorescence intensity from the sample over the Z-dimension. The long exposure Z-sweep image results in a dataset 30, shown in FIGS. 2A and 6. This data set 30 is then supplied as input to a computer or processor implementing a trained neural network model 22 (FIG. 1). This model is trained from a multitude of sets of training images, as described below, and generates a high quality, in-focus 2D projection image shown in FIGS. 3 and 6 at 140. This 2D projection image 140 (FIGS. 3, 6) contains 3D fluorescence information (since the image acquisition was obtained from integration of fluorescence intensities over the Z-dimension), but is in the form of a projection into a two dimensional, in-focus image 140. The resulting in-focus 2D projection image 140 (FIGS. 3, 6) is then used in any of the standard and known image analysis techniques, such as fluorescence object count or other fluorescence intensity metrics.

Figure 9:
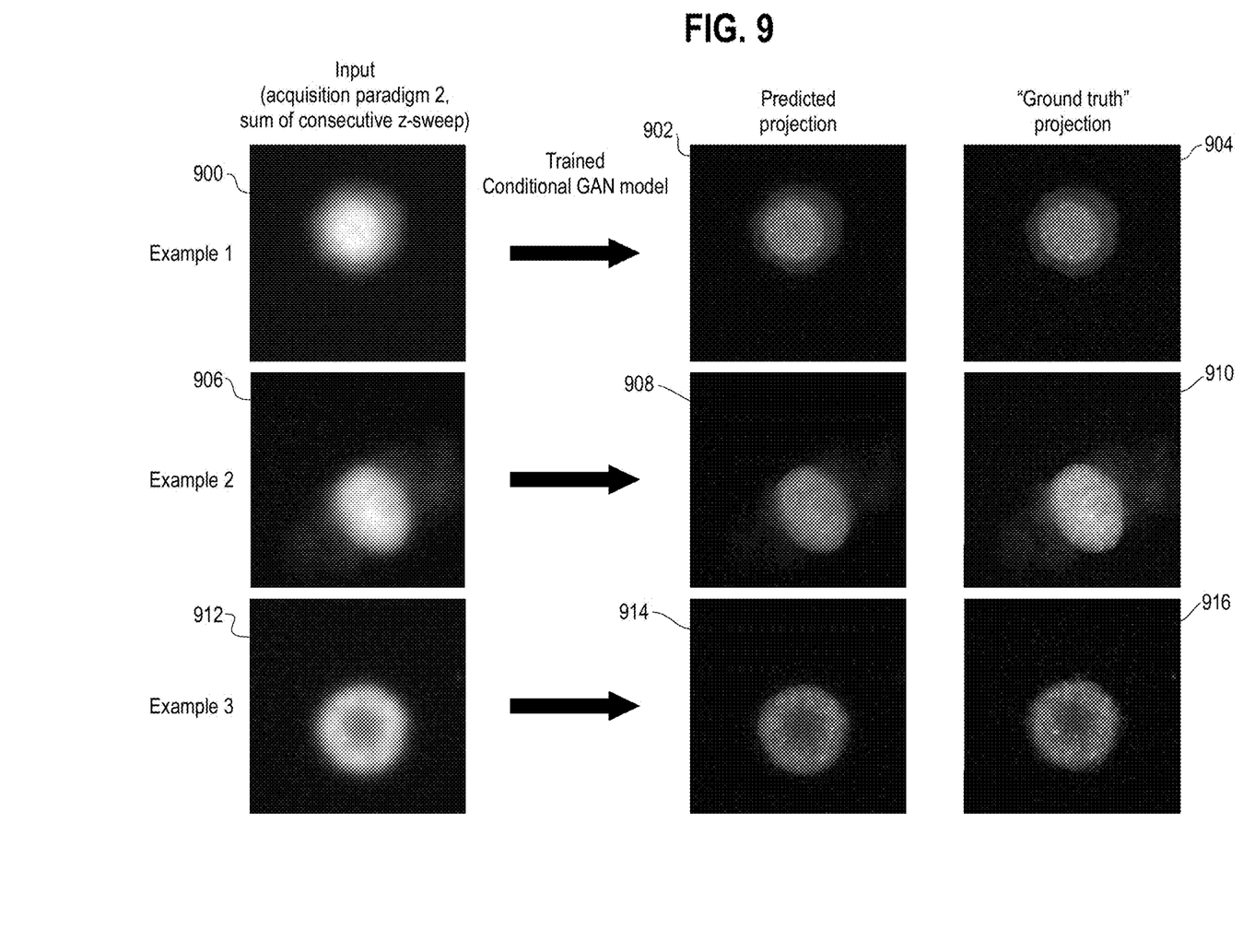
FIG. 9 is a set of three examples of an input image and model output with comparison to a ground truth projection, demonstrating the utility of the present methods.

In FIG. 2A a single long exposure Z-sweep image is acquired by exposing the camera in the fluorescence microscope continuously as the focal plane is moved in the Z-direction through the sample as indicated by the arrow 25, resulting in a two dimensional image data set 30. This is "paradigm 1" of FIG. 3. That image data set 30 is of limited usefulness for image analysis techniques due to out-of-focus issues. Hence, the trained neural network model is used to convert the out-of-focus image to a more useful, in-focus projection image as shown at 140 in FIGS. 3 and 6. Further examples are shown in FIG. 9 and will be discussed later in this document.

An alternative long exposure Z-sweep image acquisition method is shown in FIG. 2B. In this alternative, the image acquisition consists of acquiring a series of consecutive long exposure Z-sweep images, numbered 1, 2, 3 and 4 in FIG. 2B, in which the camera in the microscope is exposed and integrates fluorescence intensities over the Z-dimension while the focal plane moves through increments of the Z-dimension, and captures a series of four corresponding images or image data sets indicated at 1, 2, 3 and 4 in FIG. 2B. The series of images or image data sets are then summed to produce a single resulting long exposure Z-sweep data set or image 30. This is "paradigm 2" of FIG. 3. This image acquisition technique may have certain advantages as compared to the method of FIG. 2A, including avoiding image saturation and permitting the application of a conventional or deep learning based 2D fluorescence deconvolution algorithm for each smaller sweep (1, 2, 3, 4) prior to summation, which can remove the out-of-focus fluorescence and ultimately lead to a more accurate measurement of fluorescence intensity.

Figure 3:
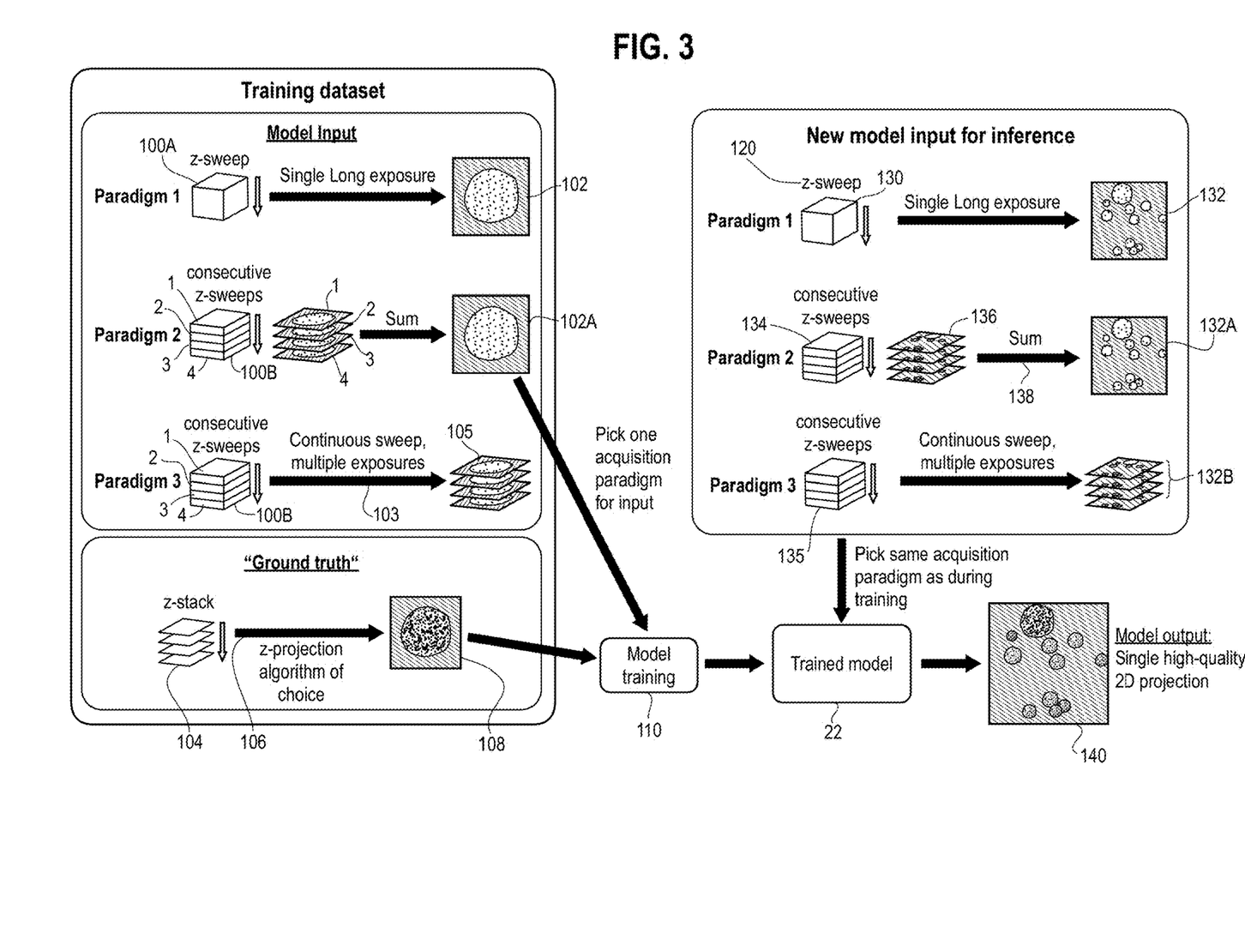
FIG. 3 is an illustration of a methodology for generating a training data set for training a neural network model.

A variation of the procedure of FIG. 2B is also possible as a third embodiment for acquiring long exposure Z-sweep images, indicated as "paradigm 3" of FIG. 3. The images 1-4 are acquired as explained above in FIG. 2B, but without the summation operation being performed. The four images are passed to the trained neural network to predict a single corresponding in-focus image from all of them. In this embodiment the four images may be combined into, in this case, a 4-channel image. The advantages listed above still apply for this embodiment. Furthermore, it may also have the advantage that it is easier for the neural network model to infer a good in-focus projection image from the images acquired in this paradigm.

FIG. 2C illustrates a prior art Z-stack image acquisition method, in which images of the sample 10 are taken at different focal planes, such as positions A, B, C and D, which results in the corresponding image datasets A, B, C and D shown in the Figure. Note that in this approach the Z dimension coordinate is fixed or stationary at the time of exposure of the camera.

Figure 6:
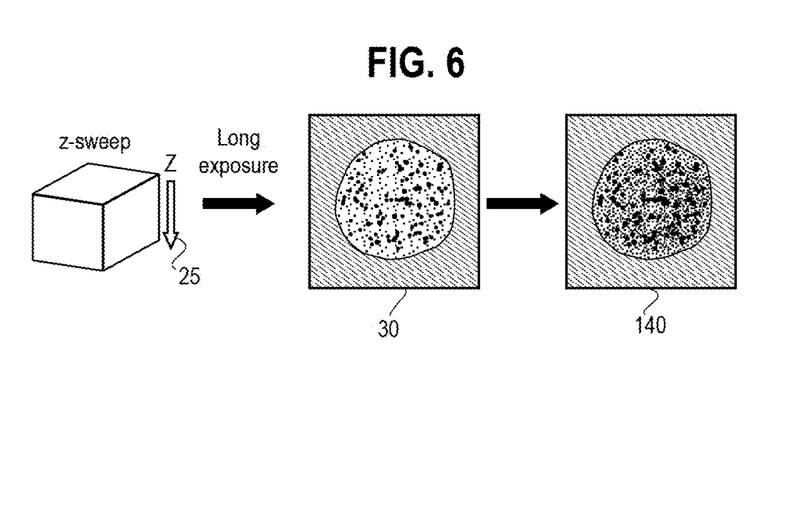
FIG. 6 is an illustration of a high quality, in-focus 2D projection image derived from a long exposure image acquisition method of FIG. 2A or 2B using a trained neural network model.

FIG. 3 shows in more detail the training of a convolutional neural network model which is used to generate the 2D projection image 140 of FIG. 6 from an input in the form of one or more long exposure Z-sweep images 30.

A training dataset for model input is prepared by generating Z-stacks 104 (procedure of FIG. 2C) and Z-sweeps (100) (procedure of either FIG. 2A, or FIG. 2B, any of the three paradigms discussed above) of the same 3D live-cell training sample. Additionally a ground truth image 108 of the same training sample is obtained from the Z-stacks 104 and a Z-projection algorithm 106. Thus, using a Z-projection algorithm of choice, such as the ImageJ algorithm cited previously, the Z-stacks 104 are used to generate a high-quality 2D projection 108 that will serve as the "ground truth" for the model training. Z-sweep images 102, 102A or 105 are used as input for model training along with the associated ground truth 108. These pairs of data (actually, thousands of such pairs) are used to train a convolutional neural network (CNN) model as indicated at 110 in order to enable the network to learn how to generate a high-quality 2D projection image (140, FIG. 6) from a long-exposure Z-sweep image (30, FIG. 6). The trained neural network model is indicated at 22 in FIGS. 1 and 3. As noted above, the input to model training 110 could be the pairs of images as just described, e.g., in a supervised model training exercise, but as explained above model input need not be in pairs, as in the case of cycle-consistency loss or generative adversarial network models, using simple sets of images from the two domains (ground truth Z-projection images and Z-sweeps).

The neural network model 22 may be a supervised model, for instance an encoder-decoder based model, for example U-net, see Ronneberger, et al., "*U-net: Convolutional networks for biomedical image segmentation*", published by Springer in conjunction with the international conference on medical image computing and computer-assisted intervention (MICCAI) pp. 234-241), also published as arXiv: 1505.04597 (2015), the content of which is incorporated by reference herein. This supervised model is trained to predict the high-quality projection image directly from the corresponding long exposure Z-sweep image.

The neural network model 22 may also be designed and trained with an adversarial approach, for example a GAN, see Goodfellow et al., "*Generative Adversarial Nets,*" in Advances in Neural Information Processing Systems 27, Z. Ghahramani, M. Welling, C. Cortes, N. D. Lawrence, and K. Q. Weinberger, Eds. Curran Associates, Inc., 2014, pp. 2672-2680, where one network, a generator will be trained against another network, a discriminator. The discriminator is tasked to distinguish between real high-quality projections and the output of the generator, and the generator will be tasked with making the output indistinguishable from the real projections (i.e., ground truth).

Another alternative model architecture is conditional GAN, and will be described in further detail in conjunction with FIG. 10.

The trained neural network model 22 may also be trained using a cycle consistency loss methodology, for example CycleGAN, see Zhu, Jun-Yan, et al. "Unpaired image-to-image translation using cycle-consistent adversarial networks", Proceedings of the IEEE international conference on computer vision (2017), also published as arXiv: 1703.10593 (2017), the content of which is incorporated by reference herein, meaning that unpaired Z-sweep images are transformed into high-quality projections and then back to Z-sweep images again, and the network is trained to minimize the cycled-back reconstruction error. The advantage of using cycle-consistency is that such training does not require perfect registration between the Z-sweep image and the high-quality projection. It also opens up the possibility to train on unpaired data, from the two domains (Z-sweep images and Z-stack projection images in the present case).

Once the neural network model has been trained from a collection of training samples (perhaps hundreds or thousands of such 3D live-cell samples), at the time of inference, there is no longer a need to collect Z-stacks images in accordance with FIG. 2C, which is a slower process and more damaging to the sample. Rather, only one or more high-throughput long-exposure Z-sweep images are collected, using the technique of FIG. 2A or 2B, which are then input into the trained model 22 to generate the high-quality 2D projection image 140. In one embodiment indicated at 120 ("paradigm 1"), just a single Z-sweep is performed and the resulting image data set 132 is input into the trained model 22. In another embodiment indicated as "paradigm 2" in FIG. 3, a series of consecutive Z-sweeps are performed indicated at 134 (technique of FIG. 2B), producing images 136 which are summed to produce an image data set 132A. The consecutive Z-sweep images 136 have several advantages without sacrificing the speed of acquisition: (1) they avoid image saturation and (2) they permit the application of a conventional or deep learning based 2D fluorescence deconvolution algorithm for each smaller sweep prior to summation, which can removes the out-of-focus fluorescence and ultimately lead to a more accurate measurement of fluorescence intensity. The resulting images 136 are optionally subject to fluorescence deconvolution and then summing operations as indicated at 138 and the resulting image data set 132A is then supplied to the trained model 22.

In a third alternative, "paradigm 3" in FIG. 3, a set of consecutive z-sweeps 135 are performed (procedure of FIG. 2B) and a set of resulting image data sets from each of the sweeps 132B is obtained. The image data sets 132B are supplied to the trained model 22. If, in this alternative, the image data sets are combined into a single multi-channel input image as described previously it can improve the neural network output due to providing complementary features.

A model that has been trained from input images acquired according to image acquisition paradigm 1, 2 or 3 is used for model inference such that it matches the type of paradigm used to obtain the input image. In other words, if, for example, at the time of inference, the input image is acquired under paradigm 2 then the inference is performed by model trained from images which were also acquired under paradigm 2.

As a result of model interference the trained model 22 produces the model output 140, namely a single, high quality, in-focus, two-dimensional projection image.

Figure 4:
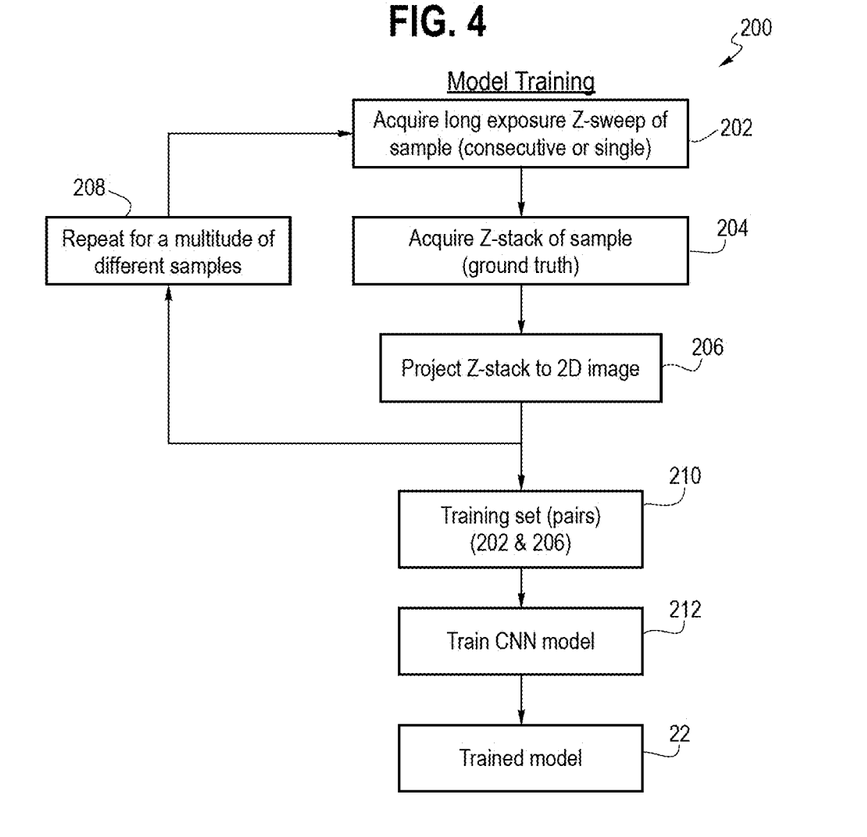
FIG. 4 is a flow chart of a model training procedure for training the neural network model of FIG. 3.

The model training will be described in more detail in FIG. 4. The model training process 200 includes a step 202 of performing a long exposure Z-sweep on a live-cell, 3D training sample, for example (using either FIG. 2A or 2B image acquisition technique), a step 204 of acquiring a Z-stack image of the same training sample using the technique of FIG. 2C, and projecting the Z-stack acquired at step 206 into a 2D image using the Z-stack projection technique such as ImageJ. This process is repeated for a multitude of different training samples, as indicated at 208, for example thousands or even tens of thousands of live-cell, 3D samples spanning all of the expected types of samples used in a fluorescence microscope in current live-cell research. The multitude of images (from steps 202 and 206), either as pairs or unpaired sets of data from the two domains (Z-sweep images and ground truth images) are then provided as a training set 210 and used to train a neural network as indicated in 212 in either a supervised learning model training exercise or a self-supervised model training exercise according the CycleGAN procedure, or a generative adversarial network approach. The result of this exercise is a trained neural network model 22.

In one possible variation, there may be several discrete models trained using this general approach, one for each type of live-cell sample, such as one for stem cells, one for oncology, one for brain cells, etc. Each model is trained from hundreds or thousands of images (paired or unpaired) obtained using the procedure set forth in FIGS. 3 and 4.

Figure 5:
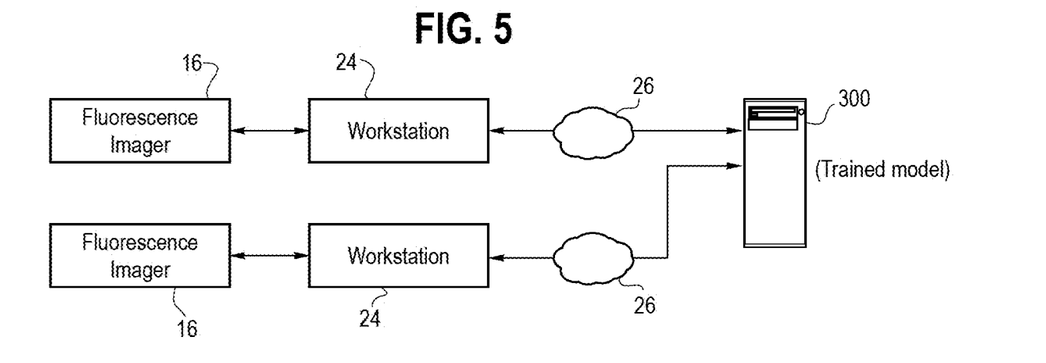
FIG. 5 is an illustration of a network embodiment in which a trained neural network model is implemented on a remote computer and communicates with remote workstations receiving fluorescence images from connected fluorescence microscopes.

Referring to FIGS. 1 and 5, it is possible that the trained neural network model 22 could be implemented in a workstation 24 or processor that is associated with or part of the fluorescence microscope/imager 16 itself. Alternatively, the trained model could be implemented in a remote server, such as shown at 300 in FIG. 5. In this configuration, the fluorescence microscope/imager 16 is connected to a workstation 24 with connectivity over computer networks 26 to the server 300. The workstation transmits the long exposure Z-sweep images to the server 300. In turn, the trained neural network model in the server performs inference as indicated in FIG. 3 and generates the 2D projection image (140, FIG. 6) and transmits this 2D projection image back over the network 26 to the workstation 24 where it is either displayed to the user or provided as input to image analysis and quantitation software pipelines running on the workstation 24.

Fluorescence Microscope System

Figure 7:
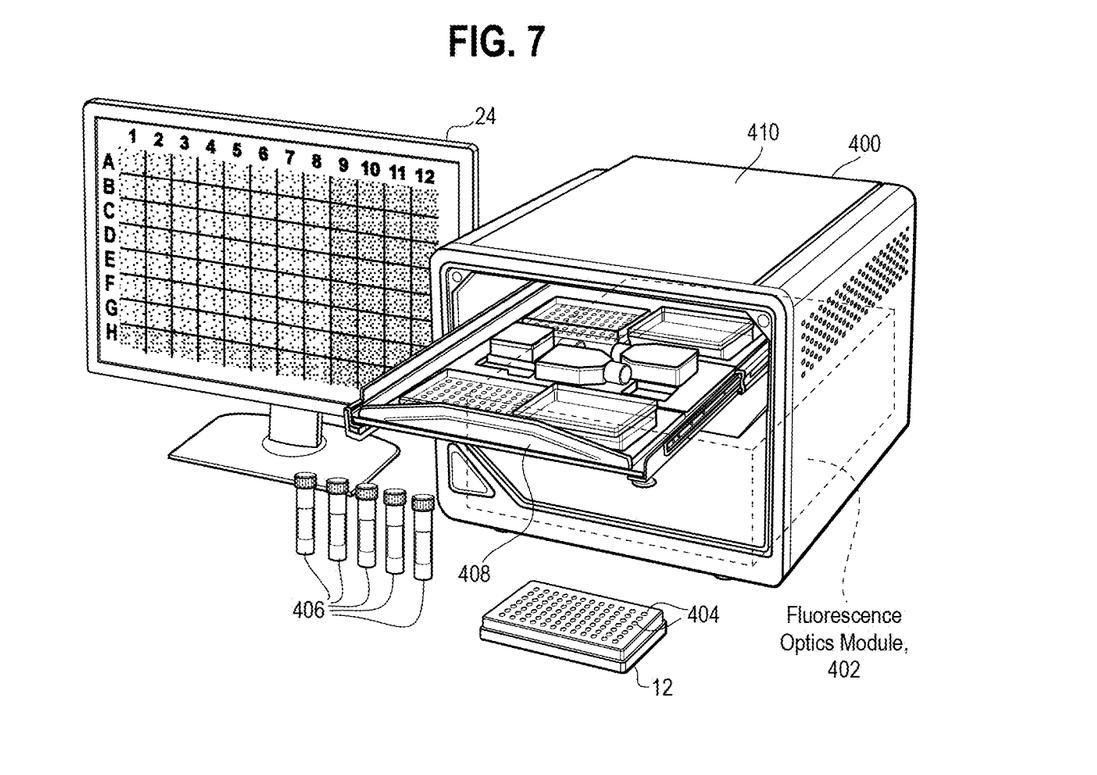
FIG. 7 is an illustration of a live cell imaging system for biological samples loaded into the sample wells of a microwell plate. The system includes a fluorescence optics module for obtaining fluorescence images of the samples in the microwell plate using features of this disclosure.

One possible implementation of the features of this disclosure is in a live-cell imaging system 400 which includes a fluorescence microscope for obtaining fluorescence images in a three-dimensional live-cell research application. FIG. 7 shows the live-cell imaging system 400 having a housing 410, the entirety of which could be placed inside a temperature and humidity controlled incubator, not shown, during use. The live-cell imaging system 400 is designed to receive microwell plates 12 which include a multitude of sample holding wells 404, each of which receives a 3D live-cell sample. The system includes a set of fluorescence reagents 406, one or more of which are added to each of the sample wells 404 so as to enable fluorescence measurements from the live-cell sample to be obtained. The system includes an associated workstation 24 which implements image analysis software and includes display features to enable the researcher to see the results of live-cell experiments conducted on the sample. The live-cell imaging system 400 includes a tray 408 which slides out of the system and allows the microwell plate 12 to be inserted onto the tray 408 and then retracts and closes so as to place the microwell plate 12 within the interior of the live-cell imaging system housing 410. The microwell plate 12 remains stationary within the housing while a fluorescence optics module 402 (see FIG. 8) moves relative to the plate 12 and obtains a series of fluorescence images over the course of an experiment. The fluorescence optics module 402 implements the long exposure Z-sweep image acquisition technique shown in FIGS. 2A and/or 2B (paradigms 1, 2 or 3 as explained previously) to generate the image dataset that is input to the trained neural network model as shown in the inference portion of FIG. 3.

Figure 8:
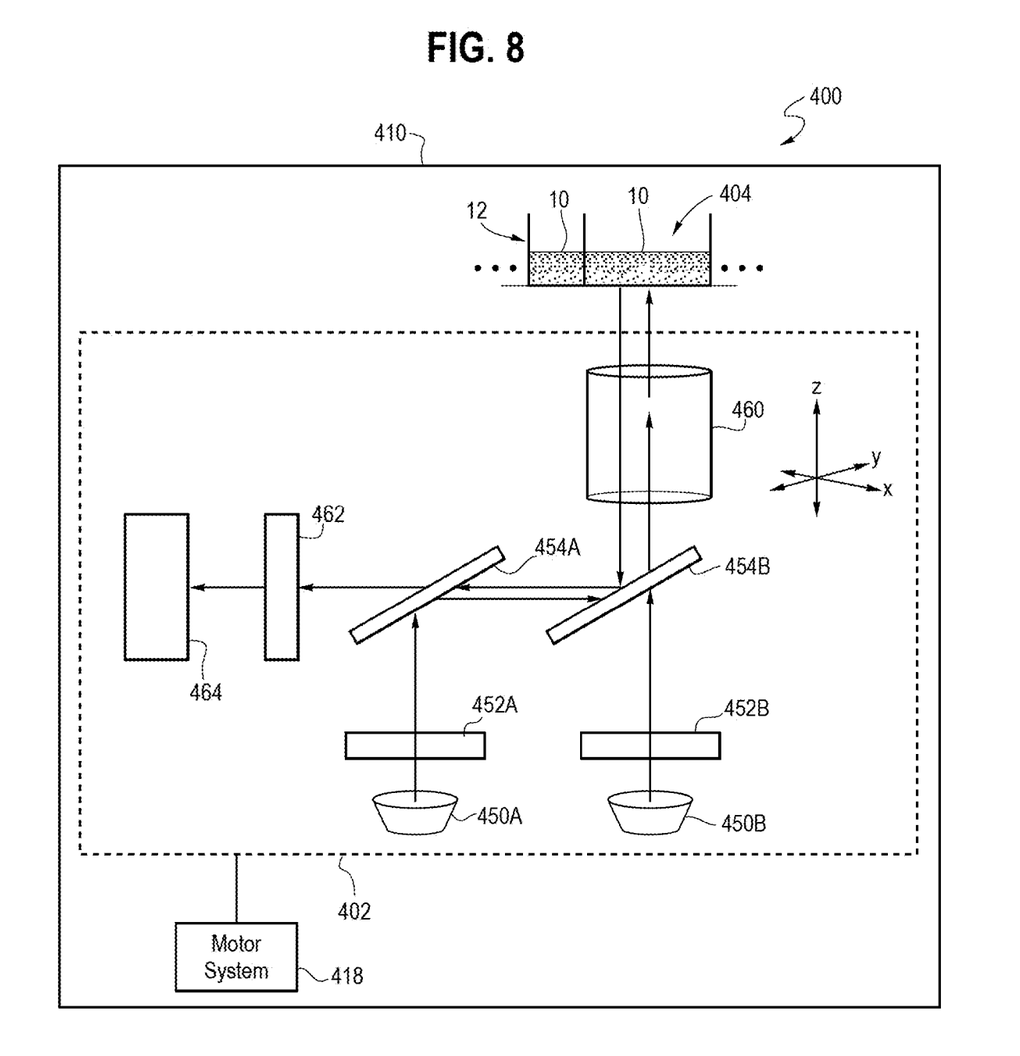
FIG. 8 is a schematic diagram of the fluorescence optics module positioned within the live cell imaging system of FIG. 7.

FIG. 8 is a more detailed optical diagram of the fluorescence optics module 402 of FIG. 7. Further details on the fluorescence optics module 402 shown in FIG. 8 can be found in US patent application of Brad Neagle et al., Ser. No. 16/854,756 filed Apr. 21, 2020, entitled "Optical module with three or more color fluorescent light sources and methods for use thereof", assigned to the assignee of this invention, the content of which is incorporated by reference herein.

The module 402 includes LED excitation light sources 450A and 450B which emit light at different wavelengths, such as 453-486 nm and 546-568 nm, respectively. The optics module 402 could be configured with a third LED excitation light source (not shown) which emits light at a third wavelength, such as 648-674 nm, or even a fourth LED excitation source at a fourth different wavelength. The light from the LEDs 450A and 450B passes through narrow bandpass filters 452A and 452B, respectively, which pass light at particular wavelengths that are designed to excite fluorophores in the sample. The light passing through the filter 452A reflects off a dichroic 454A and reflects off dichroic mirror 454B and is directed to an objective lens 460, e.g., a 20X magnifying lens. Light from LED 450B also passes through the filter 452B and also passes through the dichroic mirror 454B and is directed to the objective lens 460. The excitation light passing through the lens 460 then impinges on the bottom of the sample plate 12 and passes into the sample 10. In turn, emissions from the fluorophores in the sample pass through the lens 460, reflect off the mirror 454B, pass through the dichroic 454A, and pass through a narrow band emission filter 462 (filtering out non-fluorescence light) and impinge on a digital camera 464, which may take the form of a charge coupled device (CCD) or other type of camera currently known in the art and used in fluorescence microscopy. A motor system 418 then operates to move the entire optics module 402 in the Z-dimension to thereby acquire the long exposure Z-sweep image (FIG. 2A or 2B) while the light source 450A or 450B is in an ON state. It will be appreciated that normally only one optical channel is activated at a time, for example the LED 450A is turned on and a long exposure Z-sweep image is captured, then LED 450A is turned off and LED 450B is activated, and a second long exposure Z-sweep image is captured.

It will be appreciated that the objective lens 460 can be mounted to a turret which can be rotated about a vertical axis such that a second objective lens of different magnification is placed into the optical path to obtain a second long-exposure Z-sweep image at a different magnification. Furthermore, the motor system 418 can be configured such that it moves in the X and Y directions below the sample plate 12 such that the optical path of the fluorescence optics module 402 and the objective lens 460 is placed directly below each of the wells 404 of the sample plate 12 and fluorescence measurements as just described are obtained from each of the wells (and thus each of the live-cell samples) held in the plate 12.

The details of the motor system 418 for the fluorescence optics module 402 can vary widely and are known to persons skilled in the art.

The operation of the live-cell imaging system is under program control by a conventional computer or processing unit, including the motor system and camera which cooperate to acquire images of the samples in the sample wells. This processing unit could implement the trained neural network model of FIG. 3. In this case, as one possible embodiment, the computer includes a memory storing non-transient instructions (code) that implement the methods of this disclosure, including the image acquisition of Paradigms 1, 2, and/or 3 and the neural network model previously trained as explained above in conjunction with FIGS. 3 and 4. Similarly, the computer or processing unit includes a memory which includes instructions for generating all the training images from a set of training samples which are used for model training, and the training of the model could be done in the computer of the live-cell imaging system or in a remote computing system that implements the model and performs model training.

Applications

The methods of this document are useful for generating two-dimensional projection images of organoids, tumor spheroids, and other three-dimensional structures found in biological samples such as cell cultures. As noted previously the use of live-cell samples spans a wide variety of research areas, including immuno-oncology, oncology, metabolism, neuroscience, immunology, infectious disease, toxicology, stem cell, cardiology and inflammation. In these research areas, studies are made of cell health and proliferation, cell function, cell movement and morphology, including the study of complex immune-tumor cell interactions, synaptic activity, and metabolism in cancer cells. The methods of this disclosure are relevant to all of these applications.

In particular, the methods of this disclosure are relevant to the above applications because they allows for the high-throughput fluorescent image capture of samples, generating high-quality fluorescent 2D projection images that can be segmented and analyzed in order to measure how experimental conditions (e.g., a drug treatment) affect the health of the organoid, tumor spheroid, or other three-dimensional biological structure. Organoids (e.g., pancreatic-cell organoids, hepatic-cell organoids, intestinal-cell organoids) and tumor spheroids are of particular interest, as their three-dimensional structure more closely mimics the 'natural' three-dimensional environment of the cells being cultured. Accordingly, the reaction of organoids, tumor spheroids, or other such three-dimensional multi-cellular structures to drugs or other applied experimental conditions is likely to more closely mimic the response to corresponding samples in the human body or some other environment of interest.

Example 1

The methods of this disclosure were tested on three-dimensional live-cell biological samples using a trained conditional Generative Adversarial Network (GAN) model. The trained model produced two-dimensional, in-focus projection images, three examples of which are shown in FIG. 9. The images were obtained from samples loaded in wells of a microwell plate, using the instrumentation of FIGS. 7 and 8; the entire fluorescence imaging system and sample were positioned in an incubator which incubated the sample in appropriate temperature and humidity conditions for a live-cell culture assay.

In particular, FIG. 9 is a set of 3 examples of an input image (901, 906, 912) and model output (902, 908, 914) with comparison to a ground truth projection (904, 910, 916) obtained by a Z-stack projection algorithm, described previously, demonstrating the utility of the present methods. In FIG. 9, the input images (901, 906, 912) were generated under the second image acquisition paradigm of FIGS. 2B and 3, described in detail above. The ground truth projection images 904, 910, 916 were obtained using the methodology of FIG. 2C and a Z-stack projection algorithm.

The subject matter depicted in the images of FIG. 9 is an example of a glioblastoma cell spheroid, which is typical of a Single Tumor Spheroid assay. This assay is one of the assays available with the IncuCyte® live-cell imaging system of the assignee, depicted in FIGS. 7 and 8 of this disclosure. Further details of this assay are found at https://www.essenbioscience.com/en/applications/cell-health-viability/spheroids/. Each of the images shown in FIG. 9 is representative of an entire well of a microwell plate; the spheroid is approximately 400 μm in radius, and there is only one spheroid per well. The spheroid is a 3D structure that consists of many thousands of cells. A fluorescence label was supplied to the well to label the cell nuclei. So each one of the bright dots visible in the model output images (902, 908, 914) and in the ground truth projection (904, 910, 916) is a single cell.

The trained model that generated the model output images (902, 908, 914) in FIG. 9 was a conditional Generative Adversarial Network (GAN). Detailed information on such networks is described in Philip Isola et al., *Image-to Image Translation with Conditional Adversarial Networks*, arXiv.1611.07004 [cv.cs] (2016) and Xudong Mao, et al., *Least Squares Generative Adversarial Networks*, arXiv.1611.04076 [cv.cs] (2016), the content of both of which is incorporated by reference herein.

Figure 10:
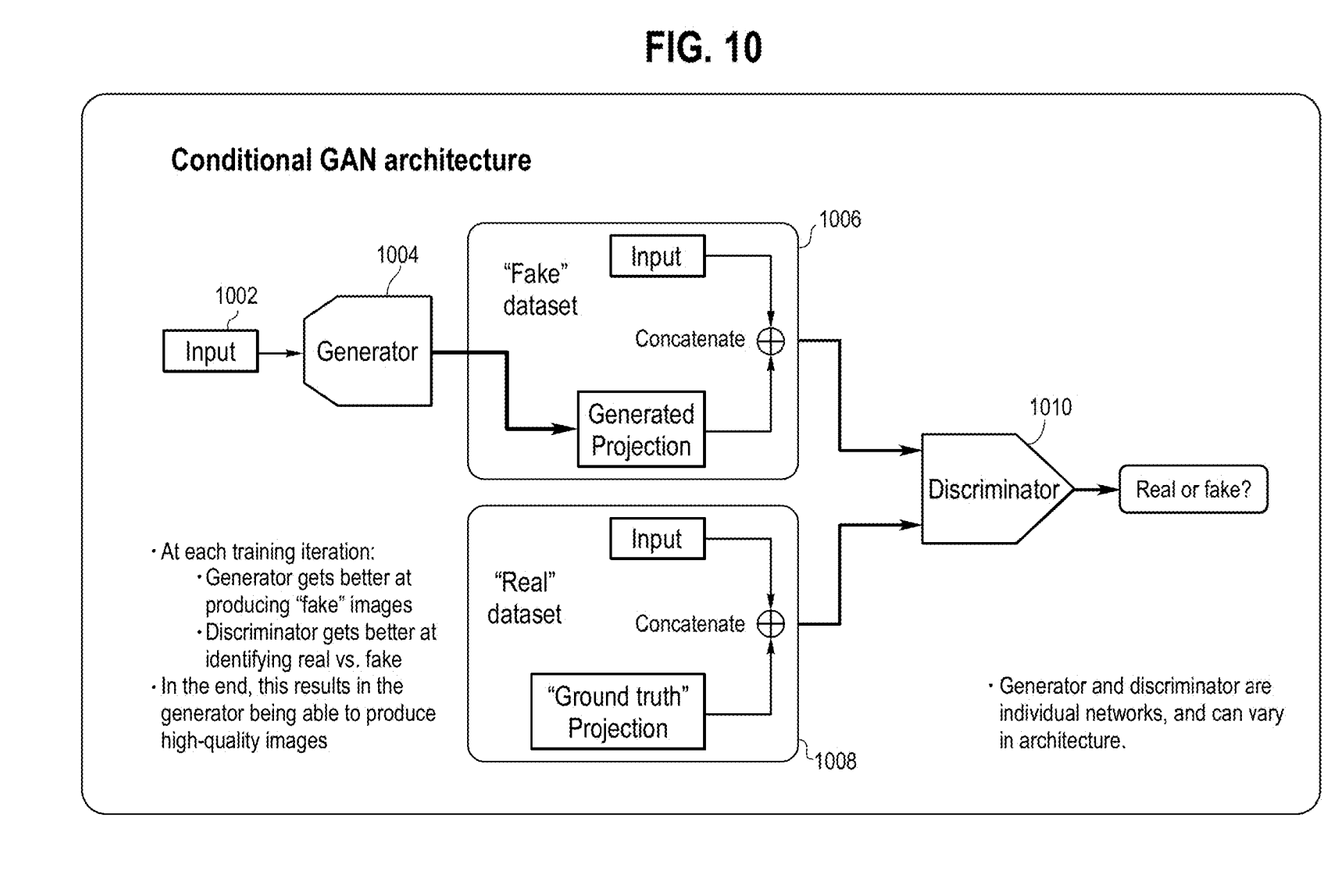
FIG. 10 is a high level architecture of the conditional GAN used to generate the model output (predicted projection) shown in FIG. 9.

A high level architecture of the conditional GAN that was used is shown in FIG. 10. As with other GANs, this model includes a generator 1004 and a discriminator 1010. The generator 1004 receives as input 1002 one of the images acquired in accordance with one of the three paradigms of FIG. 3. A "fake" dataset 1006 is generated which is a concatenation of the input image and a predicted projection image generated by the generator 1004. A "real" dataset 1008 is generated as a concatenation of the input image and a ground truth projection image. These two datasets 1006 and 1008 are then supplied to the discriminator which calculates a loss. At each training iteration, by virtue of the updating of the loss functions of the generator and discriminator, the generator 1004 gets better at producing "fake" images (i.e., the predicted projection image) and the discriminator 1010 gets better at identifying real (ground truth) v. fake (predicted projection) images. After model training, this results in the generator 1004 being able to produce high quality projection images. In the architecture of FIG. 10, the generator 1004 and discriminator 1010 are individual neural networks and can vary in their underlying architecture. In the present example, the generator 1004 is a U-net (see Ronneberger, et al., "U-net: Convolutional networks for biomedical image segmentation", published by Springer in conjunction with the international conference on medical image computing and computer-assisted intervention (MIC-CAI) pp. 234-241)), and the discriminator 1010 is a Patch-GAN, having the architecture of the Isola et al. paper cited above. Since these networks are described in detail in the scientific literature a more detailed discussion is omitted for the sake of brevity and in order to not obfuscate the inventive details of this disclosure. ResNet50 is another example of a network that can be used as the discriminator. Further detailed information on GANs is set forth in the Goodfellow et al. paper, cited previously.

In conditional GANs, the generator is conditioned on some data, such as the long exposure (Z-sweep) input images in the present case. The conditioning of the generator with the one or more long exposure images applies to both training and inference. At the end of training, only the generator is needed, as that will be utilized to generate the projection images at the time of inference. The loss function minimization and the discriminator-generator iterations is only relevant to the training phase.

The model training of a GAN is described as follows: as explained above, the GAN has two models, the Generator (G) and the Discriminator (D). The G generates output from noise; the output mimics a distribution from a training dataset. The D tries to discriminate between real and generated data. In essence, the G tries to fool the D; in each training iteration the loss functions for both the D and G are updated. Model training could be performed to update either G or D more or less frequently. The G gets better at generating data that mimics the real data from the training dataset as model training proceeds, and after model training the G can perform an inference on an input image and generate the predicted projection directly, three examples of which are shown in FIG. 9.

A few other notes on the architecture and model training of FIG. 10 are as follows. (1) Soft labels. Instead of real labels being 1, the labels can be set to be a value between [0.9, 1]. (2) Loss function. Binary Cross Entropy Loss is the original loss function of GANs. Mean squared error (MSE) loss without an activation function can be used to make it more stable (making it a Least Squares (LS) GAN). (3) No fully connected layers. If Resnet is used as the Discriminator, one can remove the last fully connected layer and input a flatten layer instead (i.e., feed it a list of labels for the loss function). (4) PatchGAN discriminator. In this embodiment of a GAN, one can use a fully-convolutional discriminator that ends up with multiple neurons for the output layer, each corresponding to a certain patch of the input image.

CONCLUSION

The methods of this disclosure overcome many of the disadvantages to conventional methods for acquiring 3D fluorescence information from a live, three-dimensional cell culture. The conventional approach of step-wise "Z-stack" fluorescence imaging of 3D samples is slow, requires user input, and ultimately exposes samples to excessive amount of fluorescent light which lead to phototoxicity and photobleaching of the sample, both of which are highly undesirable. Other approaches require specialized hardware (e.g., spinning disk) or an advanced optical setup (e.g., light sheet microscopy). Alternative deep learning approaches utilize methods that may be prone to compromising the integrity of the data, including ultra-low exposure times, or generating 3D data from a single focal plane.

Conversely, the methods of this disclosure require no specialized hardware, just a simple fluorescence microscope with an axial motor. It will be noted that the techniques described above could be readily applied to other acquisition systems. The acquisition of images from the live-cell samples is fast and has reduced risk of phototoxicity and photobleaching when compared to the conventional approach. Furthermore, the raw images collected from the camera are true representations of the fluorescence in 3D, as they are derived from fluorescence integrated over the Z-dimension. Finally, the output of a single, high-quality 2D projection image eliminates the onus on the user to have complicated software and analysis tools to handle a 3D dataset—this high-quality 2D projection (140, FIGS. 3 and 6, FIG. 9, 902, 908, 914) can be input into standard 2D image visualization, segmentation, and analysis pipelines.

We claim:

1. A method for generating an in-focus two-dimensional projection image of a fluorescence image of a three-dimensional live-cell sample, comprising the steps of:
   acquiring with a camera, one or more long exposure images of the sample by moving a focal plane of the camera through the sample in a Z direction, the camera thereby integrating fluorescence intensity from the sample over a Z-dimension;
   supplying the one or more long exposure images to a neural network model trained from a plurality of training images; and
   generating with the trained neural network model the in-focus two-dimensional projection image.

2. The method of claim 1, wherein the neural network model is selected from the group of models consisting of: a convolutional neural network (CNN) model, and an encoder-decoder based CNN model.

3. The method of claim 1, wherein the neural network model is trained in accordance of a methodology selected from the group consisting of supervised learning, a generative adversarial network (GAN) methodology, and a cycle consistency loss methodology.

4. The method of claim 3, wherein the methodology is a GAN methodology that comprises a conditional GAN having a generator and a discriminator, wherein the conditional GAN is conditioned on the one or more long exposure images.

5. The method of claim 3, wherein the methodology is a cycle consistency loss methodology, and wherein the cycle consistency loss methodology comprises CycleGAN.

6. The method of claim 1, wherein the one or more long exposure images comprises a set of consecutive long exposure images.

7. The method of claim 6, wherein the method further comprise the step of performing a fluorescence deconvolution of each of the consecutive images and a summing operation to sum the consecutive long exposure images after the fluorescence deconvolution.

8. The method claim 1, wherein the live-cell sample is contained within a well of a microwell plate.

9. The method of claim 1, wherein the plurality of training images includes one or more long-exposure images obtained by moving a focal plane of a camera through a three-dimensional live-cell training sample in a Z direction, the camera thereby integrating fluorescence intensity from the training sample over a Z-dimension, and an associated ground truth image of the three-dimensional live-cell training sample.

10. The method of claim 9, wherein the ground truth image comprises a two-dimensional projection of a set of Z-stack images of the training sample.

11. The method of claim 1, wherein the plurality of training images include one or more long-exposure images of a plurality of three-dimensional live-cell training samples selected for model training, each obtained by moving a focal plane of a camera through the training samples in a Z direction, and an associated ground truth image of each of the three-dimensional live-cell training samples, each ground truth image comprising a two-dimensional projection of a set of Z-stack images of the training sample.

12. A method for training a neural network to generate a two-dimensional projection image of a fluorescence image of a three-dimensional live-cell sample, comprising the steps of:
   (a) obtaining a training set in the form of a multitude of images, wherein the images comprise:
      (1) one or more long exposure images of the three-dimensional live-cell training sample obtained by moving a focal plane of a camera through the training sample in a Z direction, the camera thereby integrating fluorescence intensity from the training sample over a Z-dimension, and
      (2) a ground truth image, wherein the ground truth image is obtained from a set images obtained at a different Z focal plane position of the training sample and combined using a projection algorithm into a two-dimensional projection image; and
   (b) conducting a model training procedure using the training set to generate a trained neural network.

13. The method of claim 12, wherein the images (1) and (2) comprise a multitude of paired images.

14. The method of claim 12, wherein the image (1) and (2) comprise a multitude of unpaired images and wherein the model training procedure comprises a cycle consistency loss or generative adversarial network model training procedure.

15. The method of claim 12, wherein the neural network is selected from the group of networks consisting of a convolutional neural network (CNN), an encoder-decoder based CNN, a generative adversarial network (GAN), and a conditional GAN.

16. The method of claim 12, wherein the neural network comprises a conditional GAN having a generator and a discriminator, wherein the generator of the conditional GAN is conditioned on the one or more long exposure images.

17. The method of claim 12, wherein the one or more long exposure images comprises a set of consecutive images.

18. A live-cell imaging system for use in conjunction with a sample holding device adapted for holding a three-dimensional sample to generate a two-dimensional projection image of the sample, comprising:
   a fluorescence microscope having one or more excitation light sources, one or more objective lenses, and a camera operable to obtain one or more fluorescence images from the three-dimensional sample held within the sample holding device,
   wherein the fluorescence microscope includes a motor system configured to move the fluorescence microscope relative to the sample holding device in a Z direction such that the camera obtains one or more long exposure images of the sample, the images obtained by moving a focal plane of the camera through the sample in the Z direction, the camera thereby integrating fluorescence intensity from the sample over the Z-dimension; and
   a processing unit including a trained neural network model for generating the two-dimensional projection image of the three-dimensional sample from the one or more long exposure images.

19. The system of claim 18, wherein the neural network model is trained in accordance with the method of claim 12.

20. The system of claim 18, wherein the one or more long exposure images comprises a set of consecutive images.

21. The system of claim 18, wherein sample holding apparatus comprises a microwell plate having a plurality of wells.

22. The system of claim 18, wherein the neural network model is trained from plurality of training images comprising one or more long-exposure images obtained by moving a focal plane of a camera through a training sample in a Z direction, the camera thereby integrating fluorescence intensity from the training sample over a Z-dimension, and an associated ground truth image of the training sample.

23. The method of claim 1, wherein the three-dimensional live-cell sample comprises an organoid, a tumor spheroid, or a 3D cell culture.

24. The system of claim 18, wherein three-dimensional sample comprises an organoid, a tumor spheroid, or a 3D cell culture.

25. The method of claim 1, wherein the camera is incorporated in a live-cell imaging system, and wherein the trained neural network model is implemented in a computing platform remote from the live-cell imaging system and which communicates with the live-cell imaging system over a computer network.

26. The system of claim 18, further comprising a remotely-located computing platform implementing the trained neural network model and communicating with the live-cell imaging system over a computer network.

27. A method for generating a training set for training a neural network, comprising the steps of:
   (a) with a camera, acquiring one or more long exposure fluorescence images of a three-dimensional training sample by moving a focal plane of the camera through the sample in a Z direction, the camera thereby integrating fluorescence intensity from the sample over a Z-dimension;
   (b) generating a ground truth image of the same training sample from one or more different images of the training sample obtained by the camera;
   (c) repeating steps (a) and (b) for a multitude of different training samples; and
   (d) supplying the images acquired by performing steps (a), (b) and (c) as a training set for training a neural network.

28. The method of claim 27, wherein the one or more different images of the training sample obtained by the camera in step (b) comprises a set of images obtained at different Z focal plane positions of the training sample, and wherein the ground truth image is generated by projecting the set of images into a two-dimensional projection image.

29. The method of claim 27, wherein the three-dimensional sample comprises an organoid, a tumor spheroid, or a 3D cell culture.

30. The method of claim 27, further comprising the step of repeating steps (a)-(d) for different types of three-dimensional training samples thereby generating different types of training sets.

31. The method of claim 27, wherein the one or more long exposure images comprises a set of consecutive images.

32. The method of claim 31, wherein the method further comprises the step of performing a fluorescence deconvolution of each of the consecutive images and a summing operation to sum the consecutive long exposure images after the fluorescence deconvolution.

33. The method of claim 27, further comprising performing step (a) in accordance with one or more image acquisition paradigms for obtaining the long exposure images.

34. A computer-readable medium storing non-transient instructions for a live-cell imaging system including a camera and a processing unit implementing a neural network model, the instructions causing the system to perform the method of claim 1.

* * * * *